United States Patent
Ding et al.

(10) Patent No.: US 9,926,543 B2
(45) Date of Patent: Mar. 27, 2018

(54) PYROPHOSPHOROLYSIS-ACTIVATED POLYMERIZATION (PAP) USING RIBONUCLEIC ACID (RNA) TEMPLATE

(71) Applicants: Shaofeng Ding, Santa Fe Springs, CA (US); Qiang Liu, Upland, CA (US)

(72) Inventors: Shaofeng Ding, Santa Fe Springs, CA (US); Qiang Liu, Upland, CA (US)

( * ) Notice: Subject to any disclaimer, the term of this patent is extended or adjusted under 35 U.S.C. 154(b) by 297 days.

(21) Appl. No.: 14/791,474

(22) Filed: Jul. 5, 2015

(65) Prior Publication Data
US 2015/0299678 A1    Oct. 22, 2015

Related U.S. Application Data

(62) Division of application No. 13/918,980, filed on Jun. 16, 2013, now Pat. No. 9,133,491.

(60) Provisional application No. 61/724,292, filed on Nov. 8, 2012.

(51) Int. Cl.
| C12N 9/00 | (2006.01) |
| C12N 9/12 | (2006.01) |
| C12P 19/34 | (2006.01) |
| C12Q 1/68 | (2018.01) |

(52) U.S. Cl.
CPC ............ *C12N 9/1252* (2013.01); *C12P 19/34* (2013.01); *C12Q 1/68* (2013.01); *C12Q 1/6844* (2013.01)

(58) Field of Classification Search
None
See application file for complete search history.

(56) References Cited

U.S. PATENT DOCUMENTS

2002/0192663 A1 * 12/2002 Loeb .................... C12N 9/1252
435/5

FOREIGN PATENT DOCUMENTS

WO    WO 9840496 A1 * 9/1998 .......... C12N 9/1252

* cited by examiner

*Primary Examiner* — Surayaprabha Chunduru (57) ABSTRACT

A new method of RNA-PAP was developed that can directly amplify RNA template without additional treatment. RNA-PAP brings in a new mechanism for amplification of RNA template in which RNA-dependent DNA pyrophosphorolysis and RNA-dependent DNA polymerization are serially coupled using 3' blocked primers. Due to this serial coupling, RNA-PAP has high selectivity against mismatches on the RNA template, providing highly specific amplification of RNA template. In addition, mutant polymerases were genetically engineered for higher efficiency of RNA-dependent DNA pyrophosphorolysis and RNA-dependent DNA polymerization.

1 Claim, 4 Drawing Sheets

Figure 1

A. *Taq* Assay II

E. *Taq* Assay III

B. *Tth* Assay II

F. *Tth* Assay III

C. *TaqFS* Assay II

G. *TaqFS* Assay III

D. *Taq681G* Assay II

H. *Taq681G* Assay III

Figure 2

A. *TaqFS* Assay IV

E. *TaqFS* Assay V

B. 681G Assay IV

F. 681G Assay V

C. 681K Assay IV

G. 681K Assay V

D. 742S747I Assay IV

H. 742S747I Assay V

Figure 3

I. *TaqFS* Assay VI

J. 681G Assay VI

K. 681K Assay VI

L. 742S747I Assay VI

Figure 3, continued

PYROPHOSPHOROLYSIS-ACTIVATED POLYMERIZATION (PAP) USING RIBONUCLEIC ACID (RNA) TEMPLATE

CROSS-REFERENCE TO RELATED APPLICATIONS

This is a division of U.S. patent application Ser. No. 13/918,980, filed Jun. 16, 2013. This application further claims priority from U.S. provisional patent application Ser. No. 61/724,292, filed on Nov. 8, 2012.

SEQUENCE LISTING

This application is being filed along with a Sequence Listing and its electronic format entitled SequenceListing.txt.

BACKGROUND

The present invention relates to the field of molecular biology and particularly to methods for amplification of ribonucleic acid (RNA).

PAP Technology for Amplification of DNA Template

Pyrophosphorolysis activated polymerization is a method for nucleic acid amplification[1,2] where pyrophosphorolysis and polymerization are serially coupled by DNA polymerase using 3' blocked primers. A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate, which reaction is called pyrophosphorolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504,221, 7,914,995, and 7,919,253.

The serial coupling of pyrophosphorolysis and extension using the 3' blocked primer in PAP results in an extremely high selectivity 1 3 because a significant nonspecific amplification (Type II error) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single-nucleotide overlap at their 3' ends[3,4]. Bi-PAP can detect one copy of a mutant allele in the presence of $10^9$ copies of the wildtype DNA without false positive amplifications.

PAP was initially tested with Tfl and Taq polymerases using DNA template of the human dopamine D1 gene[1], proving the principle that DNA-dependent DNA pyrophosphorolysis and DNA-dependent DNA polymerization can be serially coupled. The efficiency of PAP was greatly improved using TaqFS, a genetically engineered polymerase containing contain a F667Y mutation[5], which were demonstrated using other DNA templates[2,4,6].

However, no evidence has showed that PAP can work using RNA template, a long-felt but unsolved need. For PAP to work using RNA template, it is also required RNA-dependent DNA polymerization and RNA-dependent DNA pyrophosphorolysis which latter feasibility has not been demonstrated.

RNA-Dependent DNA Polymerization or Reverse Transcription Used in RT-PCR

The first step of RT-PCR is DNA polymerization or primer extension on RNA template that is catalyzed by RNA-dependent DNA polymerase or reverse transcriptase. Avian myeloblastosis virus (AMV) and moloney murine leukemia virus (MMLV) reverse transcriptases, two mesophilic retroviral transcriptases, are commonly used in this first step to convert the RNA template into its complimentary DNA (cDNA) product[7,8]. Native Taq, a thermophilic DNA polymerase, has measurable reverse transcriptase activity particularly in the presence of $Mn^{2+}$ divalent ion[9]. rTth, another thermophilic DNA polymerase, shows over 100-fold greater reverse transcriptase activity than Taq even though they have significant amino acid sequence similarity[10]. Furthermore, Taq and rTth polymerases were also genetically engineered in order for higher reverse transcriptase activity[11,12,13,14].

RNA-Dependent DNA Pyrophosphorolysis

Taq, Tfl, TaqFS, Pfu, and Vent polymerases can catalyze DNA-dependent DNA pyrophosphorolysis[1,2,3,15]. HIV and HCV reverse transcriptases were also reported to catalyze DNA-dependent DNA pyrophosphorolysis that removes 3' dideoxynucleotide from DNA primer on synthetic DNA (rather than RNA) template[16,17].

However, there was no report of RNA-dependent DNA pyrophosphorolysis of polymerase that removes 3' deoxyribonucleotide or 3' dideoxynucleotide or 3' acyclonucleotide from a primer using RNA as template.

Advantages of the Invention

It is advantageous that RNA-PAP can direct amplify RNA template without additional treatment. In addition, RNA-PAP has high selectivity against mismatches on the RNA template, providing highly specific amplification of RNA template. Furthermore, we genetically engineered mutant polymerases for higher RNA-PAP efficiency.

SUMMARY OF THE INVENTION

A new method of RNA-PAP was developed that can directly amplify RNA template. RNA-PAP brings in a new mechanism for amplification of RNA template in which RNA-dependent DNA pyrophosphorolysis and RNA-dependent DNA polymerization are serially coupled using 3' blocked primers.

The RNA-PAP method for synthesizing nucleic acid using RNA template comprises:

(a) a 3' blocked primer that has a non-extendable nucleotide at the 3' end (3' blocker) anneals to its complementary RNA template, (b) RNA-dependent DNA pyrophosphorolysis removes the 3' blocker from the 3' blocked primer to produce a 3' unblocked primer, and (c) RNA-dependent DNA polymerization extends the 3' unblocked primer.

Of the RNA-PAP method, the steps (a), (b), and (c) can be repeated until a desired level of the extended nucleic acid is achieved.

In an embodiment, the RNA-PAP method can further include a second primer in the reaction: (d) the second primer anneals to the nucleic acid product of the step (c), and (e) DNA-dependent DNA polymerization extends the second primer, thereby an exponential amplification can be achieved.

In another embodiment, the RNA-PAP method can further include a second 3' blocked primer: (f) the second 3' blocked primer anneals to the nucleic acid product of the step (c), (g)

DNA-dependent DNA pyrophosphorolysis removes the 3' blocker from the blocked primer to produce a 3' unblocked primer, and (h) DNA-dependent DNA polymerization extends the 3' unblocked primer.

Of the RNA-PAP method, steps (b) and (c) are catalyzed by a polymerase.

In a preferred embodiment, steps (b), (c), (d), (e), (g), and (h) are catalyzed by a polymerase in one reaction tube.

The polymerase may be a genetically engineered DNA polymerase selected from the group consisting of TaqFS, TaqFS681G, TaqFS681K, TaqFS681V, TaqFS681Y, TaqFS608V681G, TaqFS599V602A605A608V681G, TaqFS742S747I corresponding to Taq polymerase according to SEQ ID NO: 10.

In a preferred embodiment, the genetically engineered polymerase is selected from the group of mutants consisting of 599V, 602A, 605A, 608V, 667Y, 681G, 681K, 681V, 681R, 742S, and 747I mutations corresponding to Taq polymerase according to SEQ ID NO: 10.

In another preferred embodiment, the genetically engineered polymerase is selected from group of mutants consisting of amino acids located at 599, 602, 605, 608, 667, 681, 742, and 747 corresponding to Taq polymerase according to SEQ ID NO: 10.

DETAILED DESCRIPTION OF THE INVENTION

Terminology

Unless defined otherwise, all technical and scientific terms used herein have the same meaning as commonly understood by one of ordinary skill in the art.

PCR refers to polymerase chain reaction.

RT-PCR refers to reverse transcription polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n + PPi \rightarrow [dNMP]_{n-1} + dNTP$[18].

DNA-dependent DNA pyrophosphorolysis refers to pyrophosphorolysis of DNA using DNA template. It is the reverse reaction of DNA-dependent DNA polymerization RNA-dependent DNA pyrophosphorolysis refers to pyrophosphorolysis of DNA using RNA template. It is the reverse reaction of RNA-dependent DNA polymerization.

Polymerase refers to a polymerase characterized as polymerization or extension of deoxyribonucleic acids.

DNA-dependent DNA polymerase refers to a polymerase characterized as DNA polymerization using DNA template.

RNA-dependent DNA polymerase or reverse transcriptase refers to a polymerase characterized as DNA polymerization using RNA template.

3' blocked primer refers to an oligonucleotide with a 3' non-extendable nucleotide (3' blocker), such as a dideoxynucleotide. The 3' nucleotide could not be directly extended, but it can be removed by pyrophosphorolysis and then the unblocked primer can be extended by polymerase.

PAP refers to pyrophosphorolysis activated polymerization.

RNA-PAP refers to PAP using RNA template.

cDNA refers to a complementary DNA molecule synthesized using RNA template.

Thermostable refers to an enzyme that is heat stable or heat resistant.

Protein mutation refers to a change in amino acid residue at a location of a protein, like Taq polymerase. The change in amino acid residue is defined with respect to a naturally occurring protein. A protein having a mutation is referred to as a "mutant" protein.

Unless indicated otherwise, an amino acid position should be interpreted as the analogous position in all DNA polymerases, even though the single letter amino acid code specifically relates to the amino acid residue at the indicated position in Taq polymerase.

Principle of RNA-PAP

Figure 1:
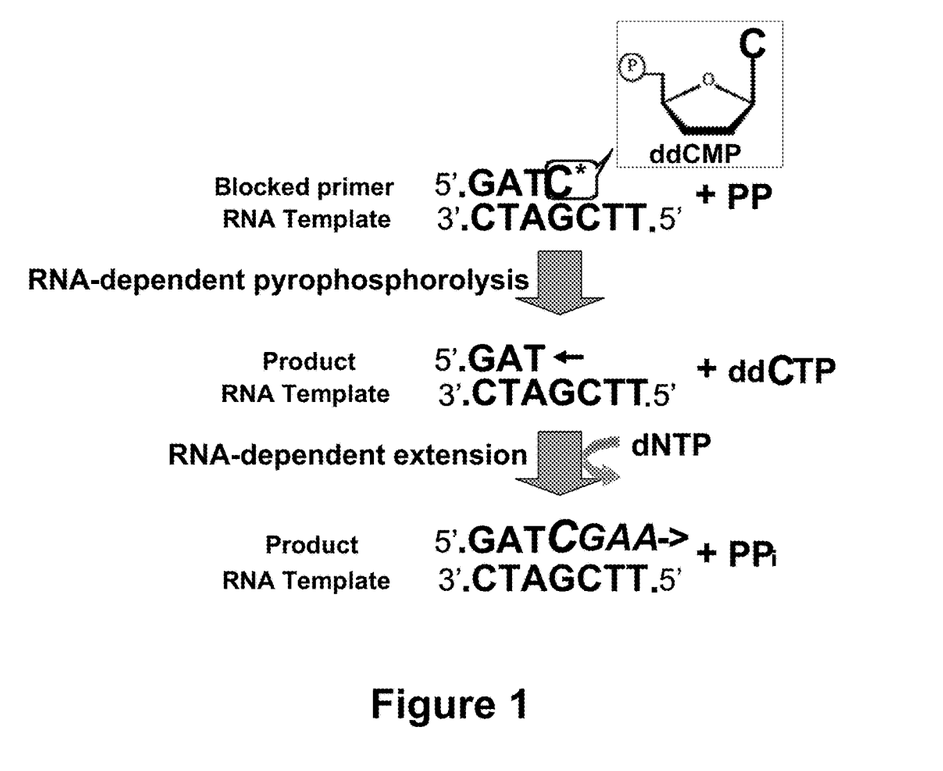
FIG. 1 illustrates the principle of RNA-PAP. The DNA primer is blocked at the 3' end with, e.g., a dideoxynucleotide, preventing it from extended by polymerase. When the 3' blocked primer anneals to its complementary RNA template, the 3' dideoxynucleotide can be removed by RNA-dependent DNA pyrophosphorolysis. Then the unblocked DNA primer can be extended on the RNA template by RNA-dependent DNA polymerization.

The invention is a RNA amplification method of synthesizing desired nucleic acid on RNA template (FIG. 1).

The method comprises the following steps: a) hybridization: annealing to the RNA template a complementary 3' blocked primer that has a 3' non-extendable nucleotide (3' blocker), b) RNA-dependent DNA pyrophosphorolysis: removing the 3' blocker from the 3' blocked primer, and c) RNA-dependent DNA polymerization: extending the 3' unblocked primer to synthesize the desired nucleic acid (FIG. 1).

The method yields a single-stranded complementary DNA (cDNA), or an RNA/cDNA duplex. Subsequent to step c, the cDNA product can be further amplified, for example, by PAP or PCR.

The method may employ a polymerase that catalyzes both RNA-dependent DNA pyrophosphorolysis and RNA-dependent DNA polymerization.

3' blockers include but not limited to 3' dideoxynucleotides. Other 3' blockers, such as acyclonucleotides that substitute a 2-hydroxyethoxymethyl group for the 2'-deoxyribofuranosyl sugar[3], may also be used.

A biological sample may contain RNA molecules. The RNA may be heterogeneous in which the target RNA is a small portion.

EXAMPLES

The practice of the present invention employs, unless otherwise indicated, common techniques of chemistry, molecular biology, and recombinant DNA, e.g., those by Sambrook et al., *Molecular Cloning*, 2nd Ed.[19]; Sambrook and Russell, *Molecular Cloning*, 3rd Ed.[20]; Ausubel et al., *Current Protocols in Molecular Biology*[21].

Example 1

Materials and Methods
Preparation of Primers

Each 3' blocked primer, 30 nucleotides long and blocked with ddCMP at the 3' end, was chemically synthesized and HPLC purified by Integrated DNA Technologies. The regular DNA primers were also synthesized by the same vendor (Table 1).

TABLE 1

List of primers and assays

| Assay | Name [b] | Sequence (5' to 3') (SEQ ID NO:) | Location | Product size (bp) | Starting template |
|---|---|---|---|---|---|
| I. PCR | P53(13280) 20D | AGGGTCCCCAGGCCTCTGAT (1) | Intron 5 | 208 | Genomic DNA |
| | P53(13488) 22U | GCCACTGACAACCACCCTTAAC (2) | Intron 6 | | |
| II. RT-PCR [a] | ACTB(426) 25D | CAACCGCGAGAAGATGACCCAGATC (3) | Exons 3 and 4 | 63 | Total RNA |
| | ACTB(488) 25U | GCAACGTACATGGCTGGGGTGTTGA (4) | Exon 4 | | |
| III. RT-PCR | ACTB(426) 25D | CAACCGCGAGAAGATGACCCAGATC (3) | Exons 3 and 4 | 280 | Total RNA |
| | ACTB(705) 25U | TTCCCGCTCGGCCGTGGTGGTGAAG (5) | Exon 4 | | |
| IV. RNA-PAP [a] | ACTB(426) 25D | CAACCGCGAGAAGATGACCCAGATC (3) | Exons 3 and 4 | 63 | Total RNA |
| | ACTB(488) 30U | GCAACGTACATGGCTGGGGTGTTGA AGGTddC (6) [c] | Exon 4 | | |
| V. RNA-PAP [a] | ACTB(426) 25D | CAACCGCGAGAAGATGACCCAGATC (3) | Exons 3 and 4 | 147 | Total RNA |
| | ACTB(572) 30U | ACAGTGTGGGTGACCCCGTCACCGG AGTCddC (7) | Exon 4 | | |
| VI. RNA-PAP [a] | GAPDH (50)-30D | ACCATGGGGAAGGTGAAGGTCGGAG TCAAddC (8) | Exon 2 | 61 | Total RNA |
| | GAPDH (110)-30U | TGGTGACCAGGCGCCCAATACGACC AAATddC (9) | Exon 3 | | |

[a] In order to avoid non-specific amplification from potentially contaminated genomic DNA, RT-PCR and RNA-PAP primers were designed to anneal to sequences of the transcript that span intron regions.
[b] For example, P53 means the human P53 gene; (13280), 5' end of the primer begins at nucleotide 13280 according to GenBank accession: x54156; D, downstream (i.e., in the direction of transcription). The ACTB mRNA is from GenBank accession: NM_001101.3. The GAPDH mRNA is from GenBank accession: AB062273.1. The precise sizes and locations of the PCR fragment can be obtained from the informative names.
[c] Due to the availability of chemical synthesis, ddC was exampled.

Total RNA Extraction

The total RNA was extracted from blood white cells using QIAamp RNA kit according to Qiagen' protocol (QIAamp RNA Blood Mini Handbook). Within the process, RNase-Free DNase was used to remove contaminated genomic DNA. The concentration of the total RNA was measured by a spectrophotometer at 260 nm. The quality was controlled with A260/A280 ratio between 1.8 and 2.1. It was stored at −20° C. until used.

Construction of Recombinant Plasmids

The amino acid sequence of the wildtype form of Taq polymerase is as described in GenBank accession AAA27507.1 (SEQ ID NO: 10). The numbering starts at the amino terminus residue. The letter is the single letter amino acid code for the amino acid residue at the indicated position.

Recombinant plasmid that encodes the wildtype form of Taq polymerase was constructed by ligating the Taq polymerase coding sequence, a 2.4 kb DNA segment from 121 nt to 2619 nt of GenBank accession J04639, into pET14b vector at the Nde I and BamH I restriction sites according to Navagen pET system user manual. Then the recombinant plasmid transformed DH5α *E. coli* cells and its plasmid DNA was extracted. The ligated Taq polymerase coding sequence was confirmed by ABI Sanger sequencing analysis.

Eight recombinant plasmids that encode mutant forms of Taq polymerase were constructed using mutagenic primers designed by QuikChange primer design program and QuikChange lightning site-directed mutagenesis kit according to Stratagene's user manual. Then each mutated plasmid transformed DH5α *E. coli* cells and its plasmid DNA was extracted. The mutant DNA sequence was confirmed by ABI Sanger sequencing analysis.

TaqFS contained G46D and F667Y mutations, TaqFS681G contained G46D, F667Y and E681G mutations, TaqFS681K contained G46D, F667Y and E681K mutations, TaqFS681V contained G46D, F667Y and E681V mutations, TaqFS681Y contained G46D, F667Y and E681Y mutations, TaqFS608V681G contained G46D, 608V, F667Y and E681G mutations, TaqFS599V602A605A608V681G contained G46D, I599V, E602A, L605A, A608V, F667Y and E681G mutations, and TaqFS742S747I contained G46D, F667Y, E742S, and M747I mutations. Individual substitution mutations are indicated by the form of a letter/number/ letter combination. The letters are the single letter code for amino acid residues. The numbers indicate the amino acid residue position of the mutation site according to SEQ ID NO: 10.

Expression and Extraction of Mutant Polymerases

The mutant Taq polymerases were expressed in transformed T7 Express lysY/I$^q$ E. coli cells according to BioLabs' manual. Before the start codon of Taq polymerase, 6×His-Tag residues were located and co-expressed. Because the expressed polymerase contained His-Tag at the N-terminus, it was purified using Qiagen Ni-NTA His-Tag technology. A typical yield of the purified polymerase was 4 mg from 500 ml of induced E. coli culture. SDS-PAGE analysis of the purified protein showed one major band of about 95,000 Daltons after Coomassie Blue staining, indicating ≥90% purity.

The enzyme was stored in the storage buffer containing 20 mM Tris-HCl (pH 8.0 at 25° C.), 100 mM KCl, 0.1 mM EDTA, 50% Glycerol, 0.5% Tween-20, and 0.5% NP-40 at −20° C. until use.

PCR to Calibrate DNA-Dependent DNA Polymerase Activity

The primers of Assay I were designed to amplify a 209-bp region of exon 6 of the human P53 gene. Each PCR mixture contained a total volume of 25 µl: 50 mM KCl, 10 mM Tris-HCl (pH 8.3), 1.5 mM $MgCl_2$, 200 µM each dNTPs (dATP, dTTP, dGTP and dCTP), 0.1 µM each primer, 0.1× SybrGreen I dye, 0.02% Twee-20, 0.02% NP-40, 20 ng of genomic DNA, and various units of polymerase.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

The cycling entailed denaturation at 94° C. for 15 seconds, annealing at 55° C. for 30 seconds, and elongation at 72° C. for 1 minute for 30 cycles. Before thermocycling, a step of 94° C. for 2 minutes was applied to completely denature the genomic DNA.

For the activity calibration, Taq polymerase (Roche) was taken as standard and its amount was 2-fold serially diluted from 1U to 1/16U in 25 µl of reaction. For comparison, other enzymes were diluted in the same way. The minimum unit of a polymerase with a measurable Ct within 30 cycles reflected its compatible level of DNA-dependent DNA polymerase activity.

To confirm the amplified product, melting curving analysis was followed from 68° C. to 95° C. with increment 0.5° C. and holding 5 seconds.

RT-PCR to Measure RNA-Dependent DNA Polymerization

Unless stated otherwise, the RT-PCR reaction mixture of 25 µl contained 880 mM Tris-HCl (pH 8.0 at 25° C.), 10 mM $(NH_4)_2SO_4$, 1.2 mM $MgCl_2$, 25 µM each dNTPs (dATP, dTTP, dGTP and dCTP), 0.1 µM each primer of Assay II or III, 90 µM $Na_4PP_i$, 0.1× SybrGreen I dye, 0.02% Twee-20, 0.02% NP-40, 1U of polymerase, and 0.25 ng of total RNA template.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

The cycling entailed 96° C. for 12 seconds, 60° C. for 30 seconds, 64° C. for 30 seconds, and 68° C. for 30 seconds for a total of 30-35 cycles. A denaturing step of 96° C. for 2 minutes was added before the first cycle.

To confirm the amplified product, melting curving analysis was followed from 68° C. to 95° C. with increment 0.5° C. and holding 5 seconds.

For further confirmation, the product was electrophoresed through a standard 3% agarose gel. The gel was stained with ethidium bromide for UV photography by a charge-coupled device camera.

RNA-PAP

Unless stated otherwise, the PAP reaction mixture of 25 µl contained 880 mM Tris-HCl (pH 8.0 at 25° C.), 10 mM $(NH_4)_2SO_4$, 1.2 mM $MgCl_2$, 25 µM each dNTPs (dATP, dTTP, dGTP and dCTP), 0.1 µM each primer of Assay IV, V, or VI, 90 µM $Na_4PP_i$, 0.1× SybrGreen I dye, 0.02% Twee-20, 0.02% NP-40, various units of polymerase, and 0.25 ng of total RNA template.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

The cycling entailed 96° C. for 12 seconds, 60° C. for 30 seconds, 64° C. for 30 seconds, and 68° C. for 30 seconds for a total of 30-35 cycles. A denaturing step of 96° C. for 2 min was added before the first cycle.

To confirm the amplified product, melting curving analysis was followed from 68° C. to 95° C. with increment 0.5° C. and holding 5 seconds to confirm the amplified product.

For further confirmation, the product was electrophoresed through a standard 3% agarose gel. The gel was stained with ethidium bromide for UV photography by a charge-coupled device camera.

Example 2

Optimal Conditions for RNA-Dependent DNA Polymerization

RT-PCR includes two steps of 1) reverse transcription of RNA template into cDNA product and 2) regular PCR amplification of the cDNA product. Reverse transcription is considered as the efficiency limiting reaction of the whole process.

In reverse transcription, AMV[7] and MMLV[8] reverse transcriptases as well as Taq[9], Tth[10] polymerases and their genetically engineered forms[11][12][13][14] are commonly used with each dNTP concentration to be 200 µm. In RT-PCR, this concentration of dNTPs is suitable to the reverse transcription step and the subsequent PCR step. However, it severely inhibited pyrophosphorolysis[1]. Thus, an optimal dNTP concentration was needed to explore.

To search for optimal reaction conditions, we designed two RT-PCR Assays II and III (Table 1). RT-PCR Assay II amplified a 63-bp ACTB mRNA region with primers ACTB(426)25D and ACTB(488)25U, and Assay III amplified a 280-bp ACTB mRNA region with primers ACTB(426)25D and ACTB(705)25U. Each assay had a forward primer and a reverse primer with the reverse primer matching the RNA template.

Figure 2:
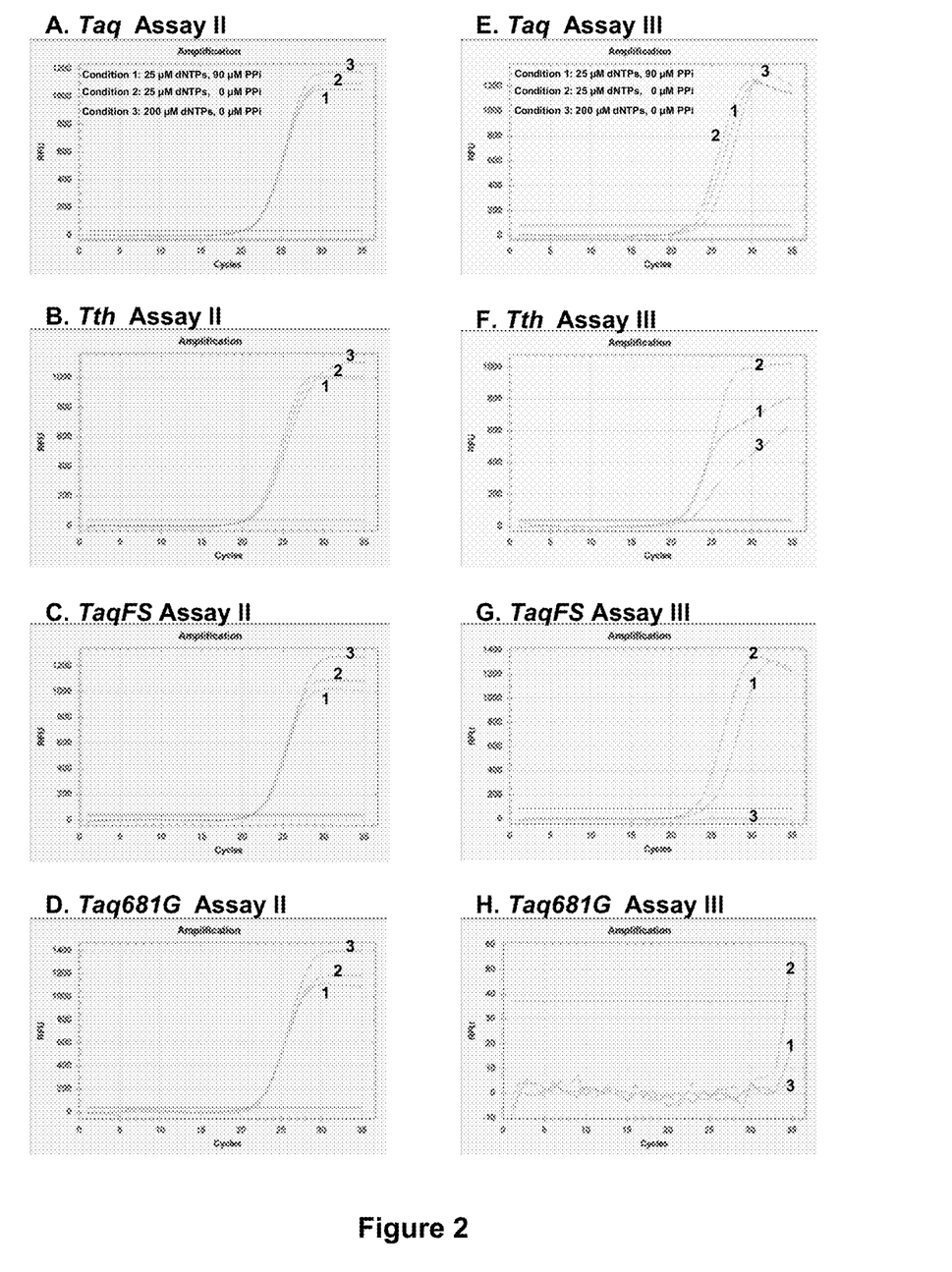
FIG. 2 illustrates optimal dNTP concentration for RNA-dependent DNA polymerization. RT-PCR Assays II (panels A to D) and III (panels E to H) amplified from 0.25 ng of total RNA in 25 μl of reaction. One Unit of each polymerases of Taq (panels A and E), rTth (panels B and F), TaqFS (panels C and G), and TaqFS742S747I (panels D and H) was used. The amplification plot is showed with cycle number and SybrGreen fluorescence unit for the given cycle.

First, we examined the effect of various dNTP concentrations in the presence of $Mg^{2+}$ divalent ion. In FIG. 2, three dNTP conditions of 25 µM each dNTP with 90 µM PPi, 25 µM each dNTP without PPi, as well as 200 µM dNTP without PPi were tested. Of four polymerases of Taq, rTth, TaqFS, and Taq681G, one unit was added to 25 µl of reaction. The polymerase activity for DNA-dependent DNA polymerization was calibrated according to Taq's activity (Roche) by amplifying a 209-bp region of exon 6 of the P53 gene (PCR Assay I) from human genomic DNA under standard PCR conditions. In addition, one unit of Taq DNA polymerase is defined as the amount of enzyme that will incorporate 10 nmol of dNTP into acid-insoluble material in 30 minutes at 75° C. (Roche). With the two RT-PCR Assays II and III, we found that the RNA-dependent DNA polymerase activity was higher with 25 μM each dNTP than with 200 μM. Thus, 25 μM rather than 200 μM each dNTP was used for the following testing.

Second, we examined the effect of various polymerase amounts. Eight polymerases of TaqFS, TaqFS681G, TaqFS681K, TaqFS681V, TaqFS681Y, TaqFS608V681G, TaqFS599V602A605A608V681G were tested. The amount of each enzyme was 2-fold serially diluted from 1U to 1/16U in 25 μl of reaction (Table 2). The minimum unit of a polymerase with a measurable Ct within 30 cycles was considered to reflect the compatible level of RNA-dependent DNA polymerization because it is the efficiency limiting reaction of the whole process. We found that the eight enzymes showed different levels of RNA-dependent DNA polymerase activity.

In addition, in melting curving analysis, only one melting peak showed the $T_m$ value from the amplified product ($T_m$=80.5-82° C. for Assays II and $T_m$=89.5-90° C. for Assay III). No-template-negative control did not show any measurable Ct.

Example 3

RNA-PAP

The process of RNA-PAP can be divided into two steps. In the first step with RNA as starting template, RNA-dependent DNA pyrophosphorolysis removes the 3' blocker from the 3' blocked primer, and then RNA-dependent DNA polymerization extends the 3' unblocked primer to generate a DNA product. In the second step with the DNA product as template, DNA-dependent DNA pyrophosphorolysis removes the 3' blocker from the 3' blocked primer and then DNA-dependent DNA polymerization extends the 3' unblocked primer. Thus, four distinct reactions are involved that can be catalyzed by a polymerase.

For proof of principle, we designed three RNA-PAP Assays IV, V, and VI (Table 1) that amplified from RNA template. Each assay had a forward primer and a reverse primer for exponential amplification. The reverse primer, blocked by a dideoxynucleotide at the 3' end, matched the RNA template.

For each assay, eight polymerases of TaqFS, TaqFS681G, TaqFS681K, TaqFS681V, TaqFS681Y, TaqFS608V681G, TaqFS599V602A605A608V681G, and TaqFS742S747I were examined. The amount of each enzyme was 2-fold serially diluted from 1U to 1/16U in 25 μl of reaction.

Figure 3:
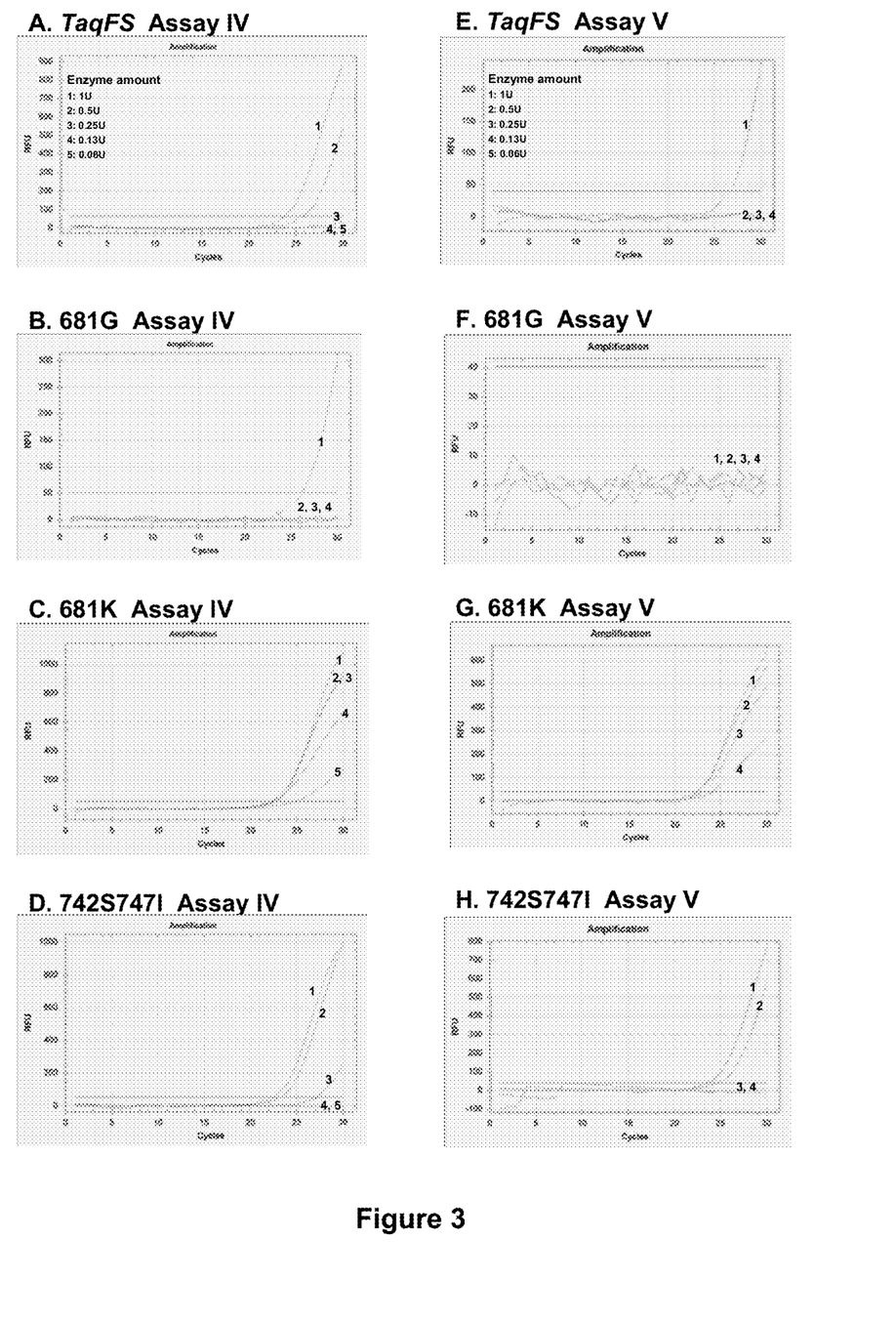
FIG. 3 illustrates RNA-PAP feasibility with various polymerases. RNA-PAP Assays IV (panels A to D), V (panels E to H) and VI (panels I to L) amplified from 0.25 ng of total RNA. For each assay, four polymerases of TaqFS (panels A, E, and I), TaqFS681G (panels B, F, and J), TaqFS681K (panels C, G, and K), and TaqFS742S747I (panels D, H, and L) were tested. The amount of each enzyme was 2-fold serially diluted from 1U to 1/16U in 25 μl of reaction.

RNA-PAP Assay VI amplified a 63-bp ACTB mRNA region with primers ACTB(426)25D and ACTB(488)30U (Table 2, FIG. 3A). In the first step, RNA-dependent DNA pyrophosphorolysis removed the 3' ddC nucleotide from the 3' blocked primer ACTB(488)30U and then RNA-dependent DNA polymerization extended the unlocked primers by 34 bases.

RNA-PAP Assay V amplified a 147-bp ACTB mRNA region with primers ACTB(426)25D and ACTB(572)30U (Table 2, FIG. 3B). In the first step, RNA-dependent DNA pyrophosphorolysis removed the 3' ddC nucleotide from the 3' blocked primer ACTB(572)30U and then RNA-dependent DNA polymerization extended the unlocked primers by 118 bases.

RNA-PAP Assay VI amplified a 61-bp GAPDH mRNA region with primers GAPDH(50)-30D and GAPDH(110)-30U (Table 2, FIG. 3C). In the first step, RNA-dependent DNA pyrophosphorolysis removed the 3' ddC nucleotide from the 3' blocked primer GAPDH(110)-30U and then RNA-dependent DNA polymerization extended the unlocked primers by 32 bases.

With Assays IV, V, and VI, we proved the principle of RNA-PAP and particularly demonstrated the feasibility of 1) RNA-dependent DNA pyrophosphorolysis and 2) the serial coupling of RNA-dependent DNA pyrophosphorolysis and RNA-dependent DNA polymerization. We also found that five enzymes of TaqFS681K, TaqFS681V, TaqFS681Y, TaqFS608V681G, and TaqFS742S747I showed higher activities particularly in RNA-dependent DNA pyrophosphorolysis.

In addition, in melting curving analysis, only one melting peak showed the $T_m$ value from the amplified product ($T_m$=80.5-81.5° C. for Assay IV, $T_m$=87.5-88° C. for Assay V, and $T_m$, =82-83° C. for Assay VI). No-template-negative control did not show any measurable Ct.

TABLE 2

The minimum units of polymerases required for RT-PCR and RNA-PAP [a]

| Polymerase | RT-PCR Assay II | RT-PCR Assay III | RNA-PAP Assay IV | RNA-PAP Assay V | RNA-PAP Assay VI |
|---|---|---|---|---|---|
| TaqFS | 0.125 U[b] | 1 U | 0.5 U | 1 U | 0.5 U |
| TaqFS681G | 0.25 U | NA | 1 U | NA | NA |
| TaqFS681K | 0.125 U | 0.25 U | 0.0625 U | 0.125 U | 0.125 U |
| TaqFS681V | 0.125 U | 0.5 U | 0.25 U | 0.5 U | 0.25 U |
| TaqFS681Y | 0.125 U | 0.5 U | 0.125 U | 0.25 U | 0.25 U |
| TaqFS608V681G | 0.125 U | 0.5 U | 0.125 U | 0.125 U | 0.0625 U |
| TaqFS599V602A605A608V681G | NA[c] | NA | 1 U | NA | NA |
| TaqFS742S747I | 0.25 U | 0.5 U | 0.25 U | 0.5 U | 0.25 U |

[a] The unit is defined as DNA-dependent DNA polymerase activity calibrated according to Taq's activity.
[b] with 0.25 ng of total RNA, the amount of enzyme was 2-fold serially diluted from 1 U to 1/16 U in 25 μl of reaction. The minimum required unit of a polymerase with a measurable Ct was counted within 30 cycles.
[c] no Ct was called within 30 cycles.

RNA-Dependent DNA Pyrophosphorolysis Vs. RNA-Dependent DNA Polymerization

The process of RNA-PAP can be divided into two steps. In the first step with RNA as starting template are two distinct reactions of RNA-dependent DNA pyrophosphorolysis and RNA-dependent DNA polymerization catalyzed serially by a polymerase.

To show their relative importance, the minimum units of polymerases were compared for RT-PCR and RNA-PAP (Table 3). In RT-PCR Assay II, RNA-dependent DNA polymerization extended 38 bases from the 3' end of the primer ACTB(488)25U. On the other hand in RNA-PAP Assay IV, RNA-dependent DNA pyrophosphorolysis removed the 3' ddC nucleotide from the 3' blocked primer ACTB(488)30U and then RNA-dependent DNA polymerization extended the unlocked primers by 34 bases. In RNA-PAP Assay VI, RNA-dependent DNA pyrophosphorolysis removed the 3' ddC nucleotide from the 3' blocked primer GAPDH(110)-30U and then RNA-dependent DNA polymerization extended the unlocked primers by 32 bases.

TABLE 3

Ratio of minimum units required for RT-PCR and RNA-PAP

| Polymerase | RT-PCR Assay II | RNA-PAP Assay IV | RNA-PAP Assay VI | Ratio of Assay II to IV | Ratio of Assay II to VI |
|---|---|---|---|---|---|
| TaqFS | 0.125 U | 0.5 U | 0.5 U | ¼ | ¼ |
| TaqFS681G | 0.25 U | 1 U | NA | ¼ | |
| TaqFS681K | 0.125 U | 0.0625 U | 0.125 U | 2 | 1 |
| TaqFS681V | 0.125 U | 0.25 U | 0.25 U | ½ | ½ |
| TaqFS681Y | 0.125 U | 0.125 U | 0.25 U | 1 | ½ |
| TaqFS608V681G | 0.0625 U | 0.125 U | 0.0625 U | ½ | ½ |
| TaqFS599V602A605A608V681G | NA | 1 U | NA | | |
| TaqFS742S747I | 0.25 U | 0.25 U | 0.25 U | 1 | 1 |

Because of the small amplicon sizes, the ratios of minimum required units between RT-PCR Assay II and RNA-PAP Assay IV or VI indicate the relative importance between RNA-dependent DNA pyrophosphorolysis and RNA-dependent DNA polymerization (Table 3). Polymerases with the ratios of minimum units to be ≥1 are preferred, such as TaqFS681K, for RNA-PAP.

REFERENCES

1. Liu, Q., and Sommer, S. S. (2000). Pyrophosphorolysis-activated polymerization (PAP): application to allele-specific amplification. BioTechniques 29, 1072-1080.
2. Liu, Q., and Sommer, S. S. (2002). Pyrophosphorolysis-activatable oligonucleotides may facilitate detection of rare alleles, mutation scanning and analysis of chromatin structures. Nucleic acids research 30, 598-604.
3. Liu, Q., and Sommer, S. S. (2004). Pyrophosphorolysis by Type II DNA polymerases: implications for pyrophosphorolysis-activated polymerization. Analytical biochemistry 324, 22-28.
4. Liu, Q., and Sommer, S. S. (2004). Detection of extremely rare alleles by bidirectional pyrophosphorolysis-activated polymerization allele-specific amplification (Bi-PAP-A): measurement of mutation load in mammalian tissues. BioTechniques 36, 156-166.
5. Tabor, S., and Richardson, C. C. (1995). A single residue in DNA polymerases of the *Escherichia coli* DNA polymerase I family is critical for distinguishing between deoxy- and dideoxyribonucleotides. Proceedings of the National Academy of Sciences of the United States of America 92, 6339-6343.
6. Shi, J., Liu, Q., and Sommer, S. S. (2007). Detection of ultrarare somatic mutation in the human TP53 gene by bidirectional pyrophosphorolysis-activated polymerization allele-specific amplification. Human mutation 28, 131-136.
7. Verma, I. M. (1977). The reverse transcriptase. Biochimica et biophysica acta 473, 1-38.
8. Roth, M. J., Tanese, N., and Goff, S. P. (1985). Purification and characterization of murine retroviral reverse transcriptase expressed in *Escherichia coli*. The Journal of biological chemistry 260, 9326-9335.
9. Jones, M. D., and Foulkes, N. S. (1989). Reverse transcription of mRNA by *Thermus aquaticus* DNA polymerase. Nucleic acids research 17, 8387-8388.
10. Myers, T. W., and Gelfand, D. H. (1991). Reverse transcription and DNA amplification by a *Thermus thermophilus* DNA polymerase. Biochemistry 30, 7661-7666.
11. Ong, J. L., Loakes, D., Jaroslawski, S., Too, K., and Holliger, P. (2006). Directed evolution of DNA polymerase, RNA polymerase and reverse transcriptase activity in a single polypeptide. Journal of molecular biology 361, 537-550.
12. Vichier-Guerre, S., Ferris, S., Auberger, N., Mahiddine, K., and Jestin, J. L. (2006). A population of thermostable reverse transcriptases evolved from *Thermus aquaticus* DNA polymerase I by phage display. Angewandte Chemie 45, 6133-6137.
13. Smith, E. S. E., C. M. Gelfand, D. H. Higuchi, R. G. Myers, T. W. Schonbrunner, N. J. Wang, A. M. (2007). High temperature reverse transcription using mutant DNA polymerases. U.S. Pat. No. 7,179,590.
14. Sauter, K. B., and Marx, A. (2006). Evolving thermostable reverse transcriptase activity in a DNA polymerase scaffold. Angewandte Chemie 45, 7633-7635.
15. Gardner, A. F., Joyce, C. M., and Jack, W. E. (2004). Comparative kinetics of nucleotide analog incorporation by vent DNA polymerase. The Journal of biological chemistry 279, 11834-11842.
16. Anion, D., Kaushik, N., McCormick, S., Borkow, G., and Parniak, M. A. (1998). Phenotypic mechanism of HIV-1 resistance to 3'-azido-3'-deoxythymidine (AZT): increased polymerization processivity and enhanced sensitivity to pyrophosphate of the mutant viral reverse transcriptase. Biochemistry 37, 15908-15917.
17. Urban, S., Fischer, K. P., and Tyrrell, D. L. (2001). Efficient pyrophosphorolysis by a hepatitis B virus polymerase may be a primer-unblocking mechanism. Proceedings of the National Academy of Sciences of the United States of America 98, 4984-4989.
18. Deutscher, M. P., and Kornberg, A. (1969). Enzymatic synthesis of deoxyribonucleic acid. 28. The pyrophosphate exchange and pyrophosphorolysis reactions of deoxyribonucleic acid polymerase. The Journal of biological chemistry 244, 3019-3028.
19. Sambrook, J. F., E. F. Maniatis, T. (1989). Molecular cloning, a laboratory manual, second edition, Cold Spring Harbor Laboratory Press, Cold Spring Harbor, N.Y.
20. Sambrook, J. (2001). Molecular Cloning: A Laboratory Manual, Third Edition, Cold Spring Harbor Laboratory Press, Cold Spring Harbor, N.Y.
21. Ausubel, F. M. (1994). Current protocols in molecular biology, John Wiley & Sons, New York

What is claimed is:

1. A purified mutant DNA polymerase for pyrophosphorolysis activated polymerization on a ribonucleic acid template comprising a 667Y mutation and another mutation selected from the group consisting of 599V, 602A, 605A, 608V, 681G, 681K, 681V, 681R, 742S and 747I mutations corresponding to Taq DNA polymerase according to SEQ ID NO: 10, wherein the mutant DNA polymerase catalyzes pyrophosphorolysis in the presence of a 3' blocked primer.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
agggtcccca ggcctctgat                                                   20

<210> SEQ ID NO 2
<211> LENGTH: 22
<212> TYPE: DNA
<213> ORGANISM: Homo sapiens

<400> SEQUENCE: 2
gccactgaca accaccctta ac                                                22

<210> SEQ ID NO 3
<211> LENGTH: 25
<212> TYPE: DNA
<213> ORGANISM: Homo sapiens

<400> SEQUENCE: 3
caaccgcgag aagatgaccc agatc                                             25

<210> SEQ ID NO 4
<211> LENGTH: 25
<212> TYPE: DNA
<213> ORGANISM: Homo sapiens

<400> SEQUENCE: 4
gcaacgtaca tggctggggt gttga                                             25

<210> SEQ ID NO 5
<211> LENGTH: 25
<212> TYPE: DNA
<213> ORGANISM: Homo sapiens

<400> SEQUENCE: 5
ttcccgctcg gccgtggtgg tgaag                                             25

<210> SEQ ID NO 6
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 6
gcaacgtaca tggctggggt gttgaaggtn                                        30
```

<210> SEQ ID NO 7
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 7
acagtgtggg tgaccccgtc accggagtcn                                        30

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 8
accatgggga aggtgaaggt cggagtcaan                                        30

<210> SEQ ID NO 9
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is dideoxyC

<400> SEQUENCE: 9
tggtgaccag gcgcccaata cgaccaaatn                                        30

<210> SEQ ID NO 10
<211> LENGTH: 832
<212> TYPE: PRT
<213> ORGANISM: Thermus aquaticus

<400> SEQUENCE: 10

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160
```

-continued

```
Tyr Leu Ile Thr Pro Ala Trp Leu Trp Glu Lys Tyr Gly Leu Arg Pro
            165                 170                 175
Asp Gln Trp Ala Asp Tyr Arg Ala Leu Thr Gly Asp Glu Ser Asp Asn
        180                 185                 190
Leu Pro Gly Val Lys Gly Ile Gly Glu Lys Thr Ala Arg Lys Leu Leu
    195                 200                 205
Glu Glu Trp Gly Ser Leu Glu Ala Leu Leu Lys Asn Leu Asp Arg Leu
210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
            245                 250                 255
Asp Phe Ala Lys Arg Arg Glu Pro Asp Arg Glu Arg Leu Arg Ala Phe
        260                 265                 270
Leu Glu Arg Leu Glu Phe Gly Ser Leu Leu His Glu Phe Gly Leu Leu
    275                 280                 285
Glu Ser Pro Lys Ala Leu Glu Glu Ala Pro Trp Pro Pro Pro Glu Gly
290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
            325                 330                 335
Glu Pro Tyr Lys Ala Leu Arg Asp Leu Lys Glu Ala Arg Gly Leu Leu
        340                 345                 350
Ala Lys Asp Leu Ser Val Leu Ala Leu Arg Glu Gly Leu Gly Leu Pro
    355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
            405                 410                 415
Trp Gly Arg Leu Glu Gly Glu Glu Arg Leu Leu Trp Leu Tyr Arg Glu
        420                 425                 430
Val Glu Arg Pro Leu Ser Ala Val Leu Ala His Met Glu Ala Thr Gly
    435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
            485                 490                 495
Glu Leu Gly Leu Pro Ala Ile Gly Lys Thr Glu Lys Thr Gly Lys Arg
        500                 505                 510
Ser Thr Ser Ala Ala Val Leu Glu Ala Leu Arg Glu Ala His Pro Ile
    515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
            565                 570                 575
```

```
Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830
```